US008168848B2

United States Patent
Lockwood et al.

(10) Patent No.: US 8,168,848 B2
(45) Date of Patent: *May 1, 2012

(54) ACCESS OPENINGS IN VACUUM BANDAGE

(75) Inventors: Jeffrey S. Lockwood, Batesville, IN (US); Robert Petrosenko, Batesville, IN (US)

(73) Assignee: KCI Medical Resources, Inc., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 10/509,137

(22) PCT Filed: Dec. 20, 2002

(86) PCT No.: PCT/US02/41210
§ 371 (c)(1),
(2), (4) Date: Sep. 27, 2004

(87) PCT Pub. No.: WO03/086232
PCT Pub. Date: Oct. 23, 2003

(65) Prior Publication Data
US 2005/0070858 A1    Mar. 31, 2005

Related U.S. Application Data

(60) Provisional application No. 60/371,618, filed on Apr. 10, 2002.

(51) Int. Cl.
*A61F 13/00* (2006.01)

(52) U.S. Cl. .......... 602/41; 604/187; 604/192; 604/268; 604/289; 604/296; 604/300; 604/304; 604/311; 604/312; 604/315; 604/316; 604/35; 604/36; 604/119

(58) Field of Classification Search ................ 604/289, 604/304–305, 307–308, 313, 315–17, 327–28, 604/540, 543; 602/41, 43, 47, 59
See application file for complete search history.

(56) References Cited

U.S. PATENT DOCUMENTS

| 765,746 A | 7/1904 | Miner |
| 774,529 A | 11/1904 | Nieschang |
| 1,000,001 A | 8/1911 | Holz |
| 1,355,846 A | 10/1920 | Rannells |

(Continued)

FOREIGN PATENT DOCUMENTS

AU    550575 A1    8/1982

(Continued)

OTHER PUBLICATIONS

Definitions of "porous" and "pore", Merriam Webster OnLine.*

(Continued)

*Primary Examiner* — Tatyana Zalukaeva
*Assistant Examiner* — Ilya Treyger
(74) *Attorney, Agent, or Firm* — Fulbright & Jaworski

(57) ABSTRACT

A wound dressing member is provided for use in a vacuum bandage connected to a vacuum source and for use with a wound having a wound surface. The member may include a top surface and a bottom surface adapted to be in contact with and generally conform to the wound surface. The member may further include a plurality of discrete holes formed in the bottom surface and at least one discrete opening formed in the top surface. A port of the member may be provided to communicate with the vacuum source, each discrete hole, and the at least one discrete opening.

11 Claims, 4 Drawing Sheets

U.S. PATENT DOCUMENTS

| | | | |
|---|---|---|---|
| 1,385,346 A | 7/1921 | Taylor | |
| 1,709,520 A | 4/1929 | Chandler | |
| 1,936,129 A | 11/1933 | Fisk | |
| 2,078,180 A | 4/1937 | Kronenberg | |
| 2,195,771 A | 4/1940 | Estler | |
| 2,221,758 A | 11/1940 | Elmquist | |
| 2,305,289 A | 12/1942 | Coburg | 128/132 |
| 2,338,339 A | 1/1944 | LaMere et al. | |
| 2,443,481 A | 6/1948 | Sene | |
| 2,547,758 A | 4/1951 | Keeling | 128/349 |
| 2,560,915 A | 7/1951 | Bamberger | 128/350 |
| 2,573,791 A | 11/1951 | Howells | |
| 2,577,945 A | 12/1951 | Atherton | |
| 2,632,443 A | 3/1953 | Lesher | |
| 2,682,873 A | 7/1954 | Evans et al. | |
| 2,910,763 A | 11/1959 | Lauterbach | 128/72.2 |
| 2,969,057 A | 1/1961 | Simmons | 128/2 |
| 3,026,874 A | 3/1962 | Stevens | |
| 3,066,672 A | 12/1962 | Crosby, Jr. et al. | 128/276 |
| 3,315,665 A | 4/1967 | MacLeod | |
| 3,367,332 A | 2/1968 | Groves | |
| 3,382,867 A | 5/1968 | Reaves | |
| 3,430,631 A | 3/1969 | Abramson | 128/350 |
| 3,492,991 A | 2/1970 | Dyer, Jr. | |
| 3,520,300 A | 7/1970 | Flower, Jr. | |
| 3,528,416 A | 9/1970 | Chamberlain | |
| 3,568,675 A | 3/1971 | Harvey | |
| 3,585,742 A | 6/1971 | Tyler | |
| 3,599,639 A | 8/1971 | Spotz | |
| 3,610,238 A | 10/1971 | Rich, Jr. | |
| 3,623,087 A | 11/1971 | Gallichotte | 340/412 |
| 3,626,087 A | 12/1971 | Tomioka | 178/5.4 |
| 3,648,692 A | 3/1972 | Wheeler | |
| 3,682,180 A | 8/1972 | McFarlane | 128/350 |
| 3,683,894 A | 8/1972 | Villari | |
| 3,721,244 A | 3/1973 | Elmaleh | |
| 3,752,158 A | 8/1973 | Kariher | |
| 3,753,439 A | 8/1973 | Brugarolas et al. | 128/350 |
| 3,782,377 A | 1/1974 | Rychlik | |
| 3,812,972 A | 5/1974 | Rosenblum | |
| 3,814,095 A | 6/1974 | Lubens | |
| 3,817,145 A | 6/1974 | Cohen | 84/471 |
| 3,823,720 A | 7/1974 | Tribble | 128/350 |
| 3,826,254 A | 7/1974 | Mellor | 128/133 |
| 3,831,588 A | 8/1974 | Rindner | |
| 3,860,008 A | 1/1975 | Miner et al. | 128/350 |
| 3,874,387 A | 4/1975 | Barbieri | |
| 3,903,882 A | 9/1975 | Augurt | |
| 3,924,624 A | 12/1975 | Schachet | 128/276 |
| 3,935,863 A | 2/1976 | Kliger | |
| 3,954,105 A | 5/1976 | Nordby et al. | |
| 3,982,546 A | 9/1976 | Friend | |
| 4,004,590 A | 1/1977 | Muriot | 128/276 |
| 4,013,076 A | 3/1977 | Puderbaugh et al. | |
| RE29,319 E | 7/1977 | Nordby et al. | |
| RE29,321 E | 7/1977 | Holbrook | 215/309 |
| 4,058,123 A | 11/1977 | May | 128/278 |
| 4,080,970 A | 3/1978 | Miller | |
| 4,096,853 A | 6/1978 | Weigand | 128/2 |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | 128/348 |
| 4,178,974 A | 12/1979 | Levin | |
| 4,184,510 A | 1/1980 | Murry et al. | 137/565 |
| 4,191,204 A | 3/1980 | Nehring | |
| 4,219,021 A | 8/1980 | Fink | 128/214 |
| 4,224,941 A | 9/1980 | Stivala | |
| 4,233,969 A | 11/1980 | Lock et al. | 128/156 |
| 4,245,630 A | 1/1981 | Lloyd et al. | 128/155 |
| 4,250,882 A | 2/1981 | Adair | |
| 4,256,109 A | 3/1981 | Nichols | 128/276 |
| 4,261,363 A | 4/1981 | Russo | 128/350 |
| 4,275,721 A | 6/1981 | Olson | |
| 4,284,079 A | 8/1981 | Adair | 128/295 |
| 4,297,995 A | 11/1981 | Golub | |
| 4,333,468 A | 6/1982 | Geist | 128/348 |
| 4,341,209 A | 7/1982 | Schaar | |
| 4,364,394 A | 12/1982 | Wilkinson | 604/96 |
| 4,373,519 A | 2/1983 | Errede et al. | |
| 4,382,441 A | 5/1983 | Svedman | |
| 4,392,853 A | 7/1983 | Muto | 604/171 |
| 4,392,858 A | 7/1983 | George et al. | 604/187 |
| 4,399,816 A | 8/1983 | Spangler | |
| 4,419,097 A | 12/1983 | Rowland | 604/174 |
| 4,445,897 A | 5/1984 | Ekbladh et al. | 604/280 |
| 4,457,755 A | 7/1984 | Wilson | |
| 4,460,370 A | 7/1984 | Allison et al. | |
| 4,465,062 A | 8/1984 | Versaggi et al. | |
| 4,465,485 A | 8/1984 | Kashmer et al. | 604/320 |
| 4,469,092 A | 9/1984 | Marshall et al. | |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,525,156 A | 6/1985 | Benusa et al. | 604/28 |
| 4,525,166 A | 6/1985 | Leclerc | |
| 4,525,374 A | 6/1985 | Vaillancourt | 427/2 |
| 4,533,352 A | 8/1985 | Van Beek et al. | |
| 4,533,419 A | 8/1985 | Pieslak et al. | |
| 4,540,412 A | 9/1985 | Van Overloop | |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | |
| 4,569,348 A | 2/1986 | Hasslinger | 604/179 |
| 4,569,674 A | 2/1986 | Phillips et al. | |
| 4,573,965 A | 3/1986 | Russo | |
| 4,579,555 A | 4/1986 | Russo | |
| 4,596,564 A | 6/1986 | Spetzler et al. | 604/281 |
| 4,605,399 A | 8/1986 | Weston et al. | |
| 4,608,041 A | 8/1986 | Nielsen | |
| 4,614,794 A | 9/1986 | Easton et al. | 530/356 |
| 4,624,656 A | 11/1986 | Clark et al. | |
| 4,633,863 A | 1/1987 | Filips et al. | |
| 4,637,819 A | 1/1987 | Ouellette et al. | |
| 4,640,688 A | 2/1987 | Hauser | 604/352 |
| 4,641,643 A | 2/1987 | Greer | |
| 4,645,492 A | 2/1987 | Weeks | |
| 4,655,210 A | 4/1987 | Edenbaum et al. | |
| 4,655,754 A | 4/1987 | Richmond et al. | |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Frysliie | |
| 4,679,590 A | 7/1987 | Hergenroeder | |
| 4,704,102 A | 11/1987 | Guthery | 604/28 |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,717,382 A | 1/1988 | Clemens et al. | |
| 4,733,659 A | 3/1988 | Edenbaum et al. | |
| 4,735,606 A | 4/1988 | Davison | |
| 4,735,610 A | 4/1988 | Akkas et al. | |
| 4,737,148 A | 4/1988 | Blake | 604/126 |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | 604/20 |
| 4,798,578 A | 1/1989 | Ranford | |
| 4,820,265 A | 4/1989 | DeSatnick et al. | |
| 4,820,284 A | 4/1989 | Hauri | |
| 4,826,494 A | 5/1989 | Richmond et al. | 604/323 |
| 4,826,949 A | 5/1989 | Stanko | 528/272 |
| 4,834,110 A | 5/1989 | Richard | |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austad | |
| 4,878,901 A | 11/1989 | Sachse | 604/174 |

| | | | | | | |
|---|---|---|---|---|---|---|
| 4,890,608 A | 1/1990 | Steer | | 5,265,605 A | 11/1993 | Afflerbach |
| 4,897,081 A | 1/1990 | Poirier et al. | | 5,275,826 A | 1/1994 | Badylak et al. ............... 424/551 |
| 4,900,302 A | 2/1990 | Newton .......................... 604/30 | | 5,278,100 A | 1/1994 | Doan et al. ..................... 437/200 |
| 4,902,508 A | 2/1990 | Badylak et al. ................. 424/95 | | 5,279,550 A | 1/1994 | Habib et al. ..................... 604/38 |
| 4,906,233 A | 3/1990 | Moriuchi et al. .............. 604/174 | | 5,281,422 A | 1/1994 | Badylak et al. ............... 424/551 |
| 4,906,240 A | 3/1990 | Reed et al. | | 5,291,887 A | 3/1994 | Stanley et al. |
| 4,915,694 A | 4/1990 | Yamamoto et al. | | 5,298,015 A | 3/1994 | Komatsuzaki et al. |
| 4,917,112 A | 4/1990 | Kalt | | 5,306,298 A | 4/1994 | Godley, III et al. |
| 4,919,654 A | 4/1990 | Kalt ............................... 604/180 | | 5,314,409 A | 5/1994 | Sarosiek et al. ............... 604/101 |
| 4,921,492 A | 5/1990 | Schultz et al. | | 5,330,452 A | 7/1994 | Zook |
| 4,930,997 A | 6/1990 | Bennett | | 5,335,651 A | 8/1994 | Foster et al. ............. 128/202.13 |
| 4,941,882 A | 7/1990 | Ward et al. | | 5,338,293 A | 8/1994 | Jeppsson et al. ................. 604/29 |
| 4,950,230 A | 8/1990 | Kendell .......................... 604/28 | | 5,342,293 A | 8/1994 | Zanger ............................ 604/22 |
| 4,953,565 A | 9/1990 | Tachibana et al. | | 5,342,301 A | 8/1994 | Saab ............................... 604/96 |
| 4,956,178 A | 9/1990 | Badylak et al. ............... 424/551 | | 5,342,376 A | 8/1994 | Ruff ............................... 606/151 |
| 4,957,492 A | 9/1990 | McVay | | 5,344,415 A | 9/1994 | DeBusk et al. |
| 4,962,761 A | 10/1990 | Golden | | 5,349,965 A | 9/1994 | McCarver |
| 4,969,880 A | 11/1990 | Zamierowski | | 5,352,463 A | 10/1994 | Badylak et al. ............... 424/551 |
| 4,969,881 A | 11/1990 | Viesturs | | 5,358,494 A | 10/1994 | Svedman |
| 4,970,298 A | 11/1990 | Silver et al. ................... 530/356 | | 5,370,610 A | 12/1994 | Reynolds ......................... 604/43 |
| 4,985,019 A | 1/1991 | Michelson ..................... 604/180 | | 5,372,821 A | 12/1994 | Badylak et al. ............... 424/551 |
| 4,988,336 A | 1/1991 | Kohn | | 5,374,254 A | 12/1994 | Buma |
| 4,990,144 A | 2/1991 | Blott | | 5,376,252 A | 12/1994 | Ekstrom et al. |
| 4,991,574 A | 2/1991 | Pocknell | | 5,380,280 A | 1/1995 | Peterson |
| 4,994,022 A | 2/1991 | Steffler et al. | | 5,395,315 A | 3/1995 | Griep |
| 4,997,425 A | 3/1991 | Shioya et al. | | 5,409,013 A | 4/1995 | Clement ......................... 128/753 |
| 5,000,172 A | 3/1991 | Ward ............................. 128/155 | | 5,413,788 A | 5/1995 | Edwards et al. ............... 424/409 |
| 5,000,741 A | 3/1991 | Kalt ............................... 604/180 | | 5,419,768 A | 5/1995 | Kayser |
| 5,002,528 A | 3/1991 | Palestrant | | 5,431,622 A | 7/1995 | Pyrozyk et al. |
| 5,002,529 A | 3/1991 | Cunningham | | 5,437,622 A | 8/1995 | Carion ............................. 602/57 |
| 5,003,971 A | 4/1991 | Buckley | | 5,437,651 A | 8/1995 | Todd et al. |
| 5,014,389 A | 5/1991 | Ogilvie et al. | | 5,439,452 A | 8/1995 | McCarty ........................ 604/248 |
| 5,034,003 A | 7/1991 | Denance | | 5,445,604 A | 8/1995 | Lang |
| 5,034,006 A | 7/1991 | Hosoda et al. | | 5,445,833 A | 8/1995 | Badylak et al. ............... 424/551 |
| 5,035,865 A | 7/1991 | Inaba et al. | | 5,447,505 A | 9/1995 | Valentine et al. ............. 604/304 |
| 5,037,397 A | 8/1991 | Kalt et al. ...................... 604/174 | | 5,449,383 A | 9/1995 | Chatelier et al. ................... 623/1 |
| 5,042,978 A | 8/1991 | Quenin et al. | | 5,451,215 A | 9/1995 | Wolter |
| 5,045,777 A | 9/1991 | Itagaki | | 5,451,373 A | 9/1995 | Lewis et al. ................. 422/82.13 |
| 5,060,662 A | 10/1991 | Farnsworth, III | | 5,478,333 A | 12/1995 | Asherman, Jr. |
| 5,071,409 A | 12/1991 | Rosenberg | | 5,484,420 A | 1/1996 | Russo |
| 5,073,172 A | 12/1991 | Fell | | 5,484,427 A | 1/1996 | Gibbons |
| 5,080,650 A | 1/1992 | Hirsch et al. .................. 604/104 | | 5,484,428 A | 1/1996 | Drainville et al. |
| 5,086,170 A | 2/1992 | Luheshi et al. ................ 540/303 | | 5,487,889 A | 1/1996 | Eckert et al. |
| 5,086,763 A | 2/1992 | Hathman | | 5,516,533 A | 5/1996 | Badylak et al. ............... 424/551 |
| 5,086,764 A | 2/1992 | Gilman | | 5,520,652 A | 5/1996 | Peterson |
| 5,092,858 A | 3/1992 | Benson et al. ................. 604/319 | | 5,527,293 A | 6/1996 | Zamierowski |
| 5,100,395 A | 3/1992 | Rosenberg ..................... 604/284 | | 5,531,670 A | 7/1996 | Westby et al. |
| 5,100,396 A | 3/1992 | Zamierowski | | 5,533,981 A | 7/1996 | Mandro et al. |
| 5,101,808 A | 4/1992 | Kobayashi et al. | | 5,534,346 A | 7/1996 | Robinson |
| 5,106,362 A | 4/1992 | Gilman | | 5,540,668 A | 7/1996 | Wilson ........................... 604/248 |
| 5,106,629 A | 4/1992 | Cartmell et al. | | 5,542,918 A | 8/1996 | Atkinson |
| 5,108,364 A | 4/1992 | Takezawa et al. ............... 604/43 | | 5,549,584 A * | 8/1996 | Gross ............................. 604/313 |
| 5,134,994 A | 8/1992 | Say ........................... 128/200.24 | | 5,554,389 A | 9/1996 | Badylak et al. ............... 424/558 |
| 5,135,518 A | 8/1992 | Vera | | 5,556,375 A | 9/1996 | Ewall |
| 5,146,925 A | 9/1992 | Snow | | 5,558,639 A | 9/1996 | Gangemi et al. ................. 604/67 |
| 5,147,338 A | 9/1992 | Lang et al. | | 5,573,784 A | 11/1996 | Badylak et al. ............... 424/551 |
| 5,149,331 A | 9/1992 | Ferdman et al. | | 5,578,022 A | 11/1996 | Scherson et al. |
| 5,152,757 A | 10/1992 | Eriksson | | 5,578,662 A | 11/1996 | Bennett et al. ................... 524/54 |
| 5,160,322 A | 11/1992 | Scheremet et al. | | 5,607,388 A | 3/1997 | Ewall |
| 5,167,613 A | 12/1992 | Karami et al. | | 5,621,035 A | 4/1997 | Lyles et al. ..................... 524/404 |
| 5,167,622 A | 12/1992 | Muto ............................... 604/35 | | 5,624,418 A | 4/1997 | Shepard |
| 5,170,781 A | 12/1992 | Loomis | | 5,628,735 A | 5/1997 | Skow |
| 5,176,502 A | 1/1993 | Sanderson et al. | | 5,629,186 A | 5/1997 | Yasukawa et al. ............. 435/177 |
| 5,176,663 A | 1/1993 | Svedman et al. | | 5,631,011 A | 5/1997 | Wadström ..................... 424/400 |
| 5,176,667 A | 1/1993 | DeBring | | 5,635,201 A | 6/1997 | Fabo |
| 5,181,908 A | 1/1993 | Bell ................................. 604/24 | | 5,636,643 A | 6/1997 | Argenta et al. |
| 5,189,609 A | 2/1993 | Tivig et al. | | 5,641,518 A | 6/1997 | Badylak et al. ............... 424/551 |
| 5,197,948 A | 3/1993 | Ghodsian ......................... 604/30 | | 5,645,081 A | 7/1997 | Argenta et al. |
| 5,215,522 A | 6/1993 | Page et al. ....................... 604/33 | | 5,645,860 A | 7/1997 | Knapp et al. ................... 424/551 |
| 5,215,539 A | 6/1993 | Schoolman | | 5,655,258 A | 8/1997 | Heintz |
| 5,224,929 A | 7/1993 | Remiszewski .................. 604/30 | | 5,656,027 A | 8/1997 | Ellingboe |
| 5,228,431 A | 7/1993 | Giarretto | | 5,662,598 A | 9/1997 | Tobin |
| 5,230,350 A | 7/1993 | Fentress | | 5,662,624 A | 9/1997 | Sundstrom et al. |
| 5,232,453 A | 8/1993 | Plass et al. ..................... 604/180 | | 5,662,625 A | 9/1997 | Westwood |
| 5,238,654 A | 8/1993 | Nohl et al. | | 5,669,892 A | 9/1997 | Keogh et al. |
| 5,249,121 A | 9/1993 | Baum et al. ................ 364/413.01 | | 5,672,152 A | 9/1997 | Mason et al. |
| 5,256,418 A | 10/1993 | Kemp et al. .................... 424/423 | | 5,674,193 A | 10/1997 | Hayes ............................... 604/28 |
| 5,261,893 A | 11/1993 | Zamierowski | | 5,678,564 A | 10/1997 | Lawrence et al. |
| 5,263,922 A | 11/1993 | Sova et al. | | 5,681,290 A | 10/1997 | Alexander .................... 604/180 |

| Patent No. | Date | Inventor | Class |
|---|---|---|---|
| 5,690,815 A | 11/1997 | Krasnoff et al. | |
| 5,695,998 A | 12/1997 | Badylak et al. | 435/391 |
| 5,697,920 A | 12/1997 | Gibbons | |
| 5,711,969 A | 1/1998 | Patel et al. | 424/551 |
| 5,718,955 A | 2/1998 | McGuire et al. | |
| 5,735,833 A | 4/1998 | Olson | |
| 5,738,656 A | 4/1998 | Wagner | 604/119 |
| 5,741,237 A | 4/1998 | Walker | |
| 5,749,842 A | 5/1998 | Cheong et al. | 602/41 |
| 5,753,267 A | 5/1998 | Badylak et al. | 424/551 |
| 5,755,791 A | 5/1998 | Whitson et al. | 623/15 |
| 5,759,570 A | 6/1998 | Arnold | |
| 5,762,640 A | 6/1998 | Kajiwara et al. | |
| 5,762,966 A | 6/1998 | Knapp et al. | 424/551 |
| 5,780,281 A | 7/1998 | Yasukawa et al. | 435/176 |
| 5,782,871 A | 7/1998 | Fujiwara et al. | |
| 5,795,584 A | 8/1998 | Totakura et al. | 424/426 |
| 5,800,383 A | 9/1998 | Chandler et al. | 604/35 |
| 5,817,145 A | 10/1998 | Augustine et al. | |
| 5,827,246 A | 10/1998 | Bowen | |
| 5,827,296 A | 10/1998 | Morris et al. | |
| 5,855,619 A | 1/1999 | Caplan et al. | 623/11 |
| 5,866,414 A | 2/1999 | Badylak et al. | 435/325 |
| 5,881,723 A | 3/1999 | Wallace et al. | |
| 5,891,111 A | 4/1999 | Ismael | 604/280 |
| 5,902,874 A | 5/1999 | Roby et al. | 528/310 |
| 5,902,875 A | 5/1999 | Roby et al. | 528/310 |
| 5,911,222 A | 6/1999 | Lawrence et al. | |
| 5,914,387 A | 6/1999 | Roby et al. | 528/310 |
| 5,919,476 A | 7/1999 | Fischer et al. | |
| 5,921,972 A | 7/1999 | Skow | |
| 5,928,174 A | 7/1999 | Gibbins | |
| 5,931,304 A | 8/1999 | Hammond | 206/570 |
| 5,941,859 A | 8/1999 | Lerman | |
| 5,942,496 A | 8/1999 | Bonadio et al. | 514/44 |
| 5,947,914 A | 9/1999 | Augustine | |
| 5,951,295 A | 9/1999 | Lyles et al. | 433/228.1 |
| 5,954,680 A | 9/1999 | Augustine | |
| 5,961,480 A | 10/1999 | Augustine | |
| 5,962,427 A | 10/1999 | Goldstein et al. | 514/44 |
| 5,964,721 A | 10/1999 | Augustine | |
| 5,964,723 A | 10/1999 | Augustine | |
| 5,986,163 A | 11/1999 | Augustine | |
| 5,997,568 A | 12/1999 | Liu | 606/228 |
| 6,010,527 A | 1/2000 | Augustine et al. | |
| 6,013,048 A | 1/2000 | Podany et al. | 604/22 |
| 6,017,493 A | 1/2000 | Cambron et al. | |
| 6,039,724 A | 3/2000 | Seifert et al. | |
| 6,045,518 A | 4/2000 | Augustine | |
| 6,045,541 A | 4/2000 | Matsumoto et al. | |
| 6,051,747 A | 4/2000 | Lindqvist et al. | 602/46 |
| 6,056,730 A | 5/2000 | Greter | |
| 6,071,254 A | 6/2000 | Augustine | |
| 6,071,267 A | 6/2000 | Zamierowski | |
| 6,071,304 A | 6/2000 | Augustine et al. | |
| 6,080,189 A | 6/2000 | Augustine et al. | |
| 6,080,243 A | 6/2000 | Insley et al. | |
| 6,093,160 A | 7/2000 | Augustine et al. | |
| 6,093,230 A | 7/2000 | Johnson et al. | |
| 6,095,992 A | 8/2000 | Augustine | |
| 6,099,567 A | 8/2000 | Badylak et al. | 623/13 |
| 6,110,197 A | 8/2000 | Augustine et al. | |
| 6,113,561 A | 9/2000 | Augustine | |
| 6,117,111 A | 9/2000 | Fleischmann | |
| 6,135,116 A | 10/2000 | Vogel et al. | |
| 6,142,982 A | 11/2000 | Hunt et al. | |
| 6,143,945 A | 11/2000 | Augustine et al. | |
| 6,149,614 A | 11/2000 | Dunshee et al. | |
| 6,171,344 B1 | 1/2001 | Atala | 623/23.64 |
| 6,174,306 B1 | 1/2001 | Fleischmann | |
| 6,203,563 B1 | 3/2001 | Fernandez | |
| 6,206,931 B1 | 3/2001 | Cook et al. | 623/23.75 |
| 6,207,875 B1 | 3/2001 | Lindqvist et al. | |
| 6,213,965 B1 | 4/2001 | Augustine et al. | |
| 6,213,966 B1 | 4/2001 | Augustine | |
| 6,217,535 B1 | 4/2001 | Augustine | |
| 6,235,009 B1 | 5/2001 | Skow | |
| 6,235,047 B1 | 5/2001 | Augustine et al. | |
| 6,241,697 B1 | 6/2001 | Augustine | |
| 6,241,698 B1 | 6/2001 | Augustine | |
| 6,241,747 B1 | 6/2001 | Ruff | 606/216 |
| 6,244,311 B1 | 6/2001 | Hand et al. | |
| 6,244,698 B1 | 6/2001 | Chino et al. | |
| 6,248,084 B1 | 6/2001 | Augustine et al. | |
| 6,254,557 B1 | 7/2001 | Augustine et al. | |
| 6,254,580 B1 | 7/2001 | Svedman | |
| 6,259,067 B1 | 7/2001 | Faries, Jr. et al. | 219/428 |
| 6,264,622 B1 | 7/2001 | Augustine | |
| 6,267,740 B1 | 7/2001 | Augustine et al. | |
| 6,283,931 B1 | 9/2001 | Augustine | |
| 6,284,941 B1 | 9/2001 | Cox et al. | |
| 6,287,316 B1 | 9/2001 | Agarwal et al. | 606/151 |
| 6,290,685 B1 | 9/2001 | Insley et al. | |
| 6,293,917 B1 | 9/2001 | Augustine et al. | |
| 6,325,798 B1 | 12/2001 | Edwards et al. | 606/41 |
| 6,345,623 B1 | 2/2002 | Heaton et al. | |
| 6,364,853 B1 | 4/2002 | French et al. | 604/35 |
| 6,394,142 B1 | 5/2002 | Woelfel et al. | 138/115 |
| 6,398,767 B1 | 6/2002 | Fleischmann | |
| 6,410,427 B1 | 6/2002 | Hu | 438/655 |
| 6,440,427 B1 | 8/2002 | Wadström | 424/400 |
| 6,458,109 B1 | 10/2002 | Henley et al. | |
| 6,471,685 B1 | 10/2002 | Johnson | |
| 6,472,581 B1 | 10/2002 | Muramatsu et al. | |
| 6,488,643 B1 | 12/2002 | Turney et al. | 602/13 |
| 6,491,682 B2 | 12/2002 | Paderni | |
| 6,491,693 B1 | 12/2002 | Lytinas | 606/53 |
| 6,493,568 B1 | 12/2002 | Bell et al. | 600/323 |
| 6,500,112 B1 | 12/2002 | Khouri | 600/38 |
| 6,520,982 B1 | 2/2003 | Boynton et al. | 607/104 |
| 6,553,998 B2 | 4/2003 | Heaton et al. | |
| 6,557,704 B1 | 5/2003 | Randolph | 206/363 |
| 6,559,773 B1 | 5/2003 | Berry | 340/815.4 |
| 6,599,277 B2 | 7/2003 | Neubert | |
| 6,626,891 B2 * | 9/2003 | Ohmstede | 604/543 |
| 6,638,270 B2 | 10/2003 | Johnson | |
| 6,648,862 B2 | 11/2003 | Watson | |
| 6,663,349 B1 | 12/2003 | Discenzo et al. | |
| 6,685,681 B2 | 2/2004 | Lockwood et al. | |
| 6,691,047 B1 | 2/2004 | Fredericks | |
| 6,695,823 B1 | 2/2004 | Lina et al. | |
| 6,695,824 B2 | 2/2004 | Howard et al. | 604/305 |
| 6,719,779 B2 | 4/2004 | Daoud | 607/105 |
| 6,749,592 B2 | 6/2004 | Lord | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph | 604/35 |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | 600/345 |
| 6,936,037 B2 | 8/2005 | Bubb et al. | 604/327 |
| 6,951,553 B2 | 10/2005 | Bubb et al. | 604/327 |
| 6,966,889 B2 | 11/2005 | Saab | 604/96.01 |
| 6,979,324 B2 | 12/2005 | Bybordi et al. | 604/313 |
| 6,994,702 B1 | 2/2006 | Johnson | 606/9 |
| 7,004,915 B2 | 2/2006 | Boynton et al. | 601/6 |
| 7,022,113 B2 | 4/2006 | Lockwood et al. | |
| 7,070,584 B2 * | 7/2006 | Johnson et al. | 604/313 |
| 7,077,832 B2 | 7/2006 | Fleischmann | 604/304 |
| 7,108,683 B2 | 9/2006 | Zamierowski | 604/304 |
| 7,117,869 B2 | 10/2006 | Heaton et al. | 128/897 |
| 7,128,735 B2 | 10/2006 | Weston | 604/543 |
| 7,144,390 B1 | 12/2006 | Hannigan et al. | |
| 7,195,624 B2 | 3/2007 | Lockwood et al. | 604/543 |
| 7,245,291 B2 | 7/2007 | Sharif et al. | 345/172 |
| 7,276,051 B1 | 10/2007 | Henley et al. | 604/304 |
| 7,338,482 B2 | 3/2008 | Lockwood et al. | 604/543 |
| 7,381,211 B2 | 6/2008 | Zamierowski | 606/215 |
| 7,422,576 B2 | 9/2008 | Boynton et al. | 607/104 |
| 7,524,286 B2 | 4/2009 | Johnson | 600/309 |
| 2001/0029956 A1 | 10/2001 | Argenta et al. | |
| 2001/0034499 A1 | 10/2001 | Sessions et al. | 602/46 |
| 2001/0043943 A1 | 11/2001 | Coffey | |
| 2001/0052681 A1 | 12/2001 | Deavila | 280/47.19 |
| 2002/0065494 A1 | 5/2002 | Lockwood et al. | |

| Pub. No. | Date | Inventor | Class |
|---|---|---|---|
| 2002/0077661 A1 | 6/2002 | Saadat | 606/221 |
| 2002/0082567 A1* | 6/2002 | Lockwood et al. | 604/307 |
| 2002/0082668 A1 | 6/2002 | Ingman | |
| 2002/0085952 A1 | 7/2002 | Ellingboe et al. | 422/45 |
| 2002/0115951 A1 | 8/2002 | Norstrem et al. | 602/27 |
| 2002/0115952 A1 | 8/2002 | Johnson et al. | |
| 2002/0120185 A1 | 8/2002 | Johnson | 600/345 |
| 2002/0143286 A1 | 10/2002 | Tumey | 604/304 |
| 2002/0161317 A1 | 10/2002 | Risk et al. | |
| 2002/0161346 A1* | 10/2002 | Lockwood et al. | 604/315 |
| 2002/0183702 A1* | 12/2002 | Henley et al. | 604/305 |
| 2002/0193723 A1 | 12/2002 | Batdorf, Sr. et al. | |
| 2003/0032951 A1 | 2/2003 | Rittman, III et al. | 606/34 |
| 2003/0077311 A1 | 4/2003 | Vyakarnam et al. | 435/41 |
| 2003/0093041 A1 | 5/2003 | Risk, Jr. et al. | 604/305 |
| 2003/0143352 A1 | 7/2003 | Yang et al. | 428/36.9 |
| 2003/0208149 A1 | 11/2003 | Coffey | |
| 2003/0219469 A1 | 11/2003 | Johnson et al. | 604/500 |
| 2004/0030304 A1 | 2/2004 | Hunt et al. | |
| 2004/0064111 A1 | 4/2004 | Lockwood et al. | |
| 2004/0167482 A1 | 8/2004 | Watson | 604/317 |
| 2004/0243073 A1 | 12/2004 | Lockwood et al. | |
| 2004/0249353 A1 | 12/2004 | Risks, Jr. et al. | |
| 2004/0260230 A1 | 12/2004 | Randolph | 604/28 |
| 2005/0004534 A1 | 1/2005 | Lockwood et al. | |
| 2005/0010153 A1 | 1/2005 | Lockwood et al. | |
| 2005/0033197 A1 | 2/2005 | Cottler | 600/573 |
| 2005/0065484 A1 | 3/2005 | Watson, Jr. | 604/289 |
| 2005/0070858 A1 | 3/2005 | Lockwood et al. | |
| 2005/0085795 A1 | 4/2005 | Lockwood et al. | |
| 2005/0090787 A1 | 4/2005 | Risk, Jr. et al. | |
| 2005/0131327 A1 | 6/2005 | Lockwood et al. | |
| 2005/0177190 A1 | 8/2005 | Zamierowski | 606/215 |
| 2005/0182445 A1 | 8/2005 | Zamierowski | 606/213 |
| 2005/0182446 A1 | 8/2005 | DeSantis | 606/222 |
| 2005/0234485 A1 | 10/2005 | Seegert et al. | 606/131 |
| 2005/0234510 A1 | 10/2005 | Zamierowski | 606/215 |
| 2005/0240220 A1 | 10/2005 | Zamierowski | 606/215 |
| 2005/0283105 A1 | 12/2005 | Heaton et al. | 128/897 |
| 2006/0015087 A1 | 1/2006 | Risk, Jr. et al. | |
| 2006/0029650 A1 | 2/2006 | Coffey | |
| 2006/0029675 A1 | 2/2006 | Ginther | 424/400 |
| 2006/0041247 A1 | 2/2006 | Petrosenko et al. | |
| 2006/0079852 A1 | 4/2006 | Bubb et al. | 604/289 |
| 2006/0129137 A1 | 6/2006 | Lockwood et al. | |
| 2006/0149170 A1 | 7/2006 | Boynton et al. | 601/6 |
| 2006/0149171 A1 | 7/2006 | Vogel et al. | 601/11 |
| 2006/0173364 A1 | 8/2006 | Ganapathy et al. | 600/364 |
| 2006/0189910 A1 | 8/2006 | Johnson et al. | 602/43 |
| 2006/0213527 A1 | 9/2006 | Argenta et al. | 128/897 |
| 2007/0005028 A1 | 1/2007 | Risk, Jr. et al. | |
| 2007/0014837 A1 | 1/2007 | Johnson et al. | 424/443 |
| 2007/0021697 A1 | 1/2007 | Ginther et al. | 602/1 |
| 2007/0021698 A1 | 1/2007 | Fleischmann | 602/2 |
| 2007/0032778 A1 | 2/2007 | Heaton et al. | |
| 2007/0038172 A1 | 2/2007 | Zamierowski | |
| 2007/0156104 A1 | 7/2007 | Lockwood et al. | 604/305 |
| 2010/0063483 A1 | 3/2010 | Adahan | 604/543 |

FOREIGN PATENT DOCUMENTS

| | | |
|---|---|---|
| AU | 745271 | 4/1999 |
| AU | 755496 | 2/2002 |
| CA | 1127488 | 7/1982 |
| CA | 2005436 | 6/1990 |
| CA | 2303085 | 3/1999 |
| DE | 0372727 | 3/1923 |
| DE | 26 40 413 A1 | 3/1978 |
| DE | 28 09 828 A1 | 9/1978 |
| DE | 3102674 A1 | 9/1982 |
| DE | 3539533 A1 | 5/1987 |
| DE | 40 12 232 | 10/1991 |
| DE | 4111122 A1 | 4/1993 |
| DE | 43 06 478 A1 | 9/1994 |
| DE | 29504378 U1 | 10/1995 |
| DE | 297 15 634 | 11/1997 |
| DE | 19722075 C1 | 10/1998 |
| DK | 64055 | 10/1945 |
| EP | 0 100 148 A1 | 2/1984 |
| EP | 0117632 A2 | 9/1984 |
| EP | 0 161 865 A2 | 11/1985 |
| EP | 0 358 302 A2 | 3/1990 |
| EP | 0424165 A1 | 4/1991 |
| EP | 0485657 A1 | 5/1992 |
| EP | 0547496 A1 | 6/1993 |
| EP | 0 730 845 | 9/1996 |
| EP | 0853 950 A1 | 7/1998 |
| EP | 0 777 504 B1 | 10/1998 |
| EP | 1 088 569 A2 | 4/2001 |
| EP | 1 100 574 | 5/2001 |
| EP | 1 190 732 A1 | 3/2002 |
| EP | 1 018 967 B1 | 8/2004 |
| EP | 1726276 | 11/2006 |
| FR | 500253 | 3/1920 |
| FR | 1303238 | 7/1962 |
| GB | 3090 | 6/1902 |
| GB | 641061 | 8/1950 |
| GB | 692578 | 6/1953 |
| GB | 1549756 | 8/1979 |
| GB | 1584772 | 2/1981 |
| GB | 2 195 255 A | 4/1988 |
| GB | 2 197 789 A | 6/1988 |
| GB | 2220357 A | 1/1990 |
| GB | 2 235 877 A | 3/1991 |
| GB | 2307180 | 5/1997 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 6/2000 |
| GB | 2351025 A | 12/2000 |
| GB | 2356148 | 5/2001 |
| HU | 199304 B | 1/1989 |
| HU | 51150 | 4/1990 |
| HU | 205557 B | 4/1990 |
| HU | 61492 | 1/1993 |
| HU | 3783 | 7/1996 |
| HU | 76351 | 8/1997 |
| HU | 215563 B | 8/1997 |
| HU | 1666 | 12/1999 |
| JP | 57-177758 | 11/1982 |
| JP | 4-129536 | 4/1992 |
| JP | H6-14995 | 1/1994 |
| JP | 6-327761 | 11/1994 |
| JP | H10-504484 | 5/1998 |
| JP | 2001-283352 | 10/2001 |
| JP | 2001-524850 | 12/2001 |
| SE | 84485 | 10/1935 |
| SG | 71559 | 4/2002 |
| SU | 587941 | 7/1978 |
| SU | 1268175 A1 | 11/1986 |
| WO | WO 80/02182 | 10/1980 |
| WO | WO 87/04626 | 8/1987 |
| WO | WO 89/04158 | 5/1989 |
| WO | WO 90/10424 | 9/1990 |
| WO | WO 90/11795 | 10/1990 |
| WO | WO 91/00718 | 1/1991 |
| WO | WO 91/08793 | 6/1991 |
| WO | WO 91/16030 | 10/1991 |
| WO | WO 92/12750 | 8/1992 |
| WO | WO 92/19313 | 11/1992 |
| WO | WO 92/20299 | 11/1992 |
| WO | 93/09727 | 5/1993 |
| WO | WO 93/09715 | 5/1993 |
| WO | WO 93/09727 | 5/1993 |
| WO | WO 94/00090 | 1/1994 |
| WO | WO 94/20041 | 9/1994 |
| WO | 96/05873 | 2/1996 |
| WO | WO 96/15745 | 5/1996 |
| WO | WO 97/18007 | 5/1997 |
| WO | WO 9718007 A1 * | 5/1997 |
| WO | WO 98/02205 | 1/1998 |
| WO | 98/38944 | 9/1998 |
| WO | 99/01173 | 1/1999 |
| WO | WO 99/13793 | 3/1999 |
| WO | WO 99/23990 | 5/1999 |
| WO | 99/59816 | 11/1999 |
| WO | WO 00/07653 | 2/2000 |
| WO | WO 00/15277 | 3/2000 |

| | | |
|---|---|---|
| WO | 00/21586 | 4/2000 |
| WO | WO 00/21586 | 4/2000 |
| WO | WO 00/28890 | 5/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | 01/85248 | 11/2001 |
| WO | 01/89431 | 11/2001 |
| WO | WO 01/85248 A1 | 11/2001 |
| WO | WO 01/89431 | 11/2001 |
| WO | WO 02/38091 | 5/2002 |
| WO | WO 02/43634 | 6/2002 |
| WO | 03/005943 | 1/2003 |
| WO | 03/045492 | 6/2003 |
| WO | WO 03/057071 | 7/2003 |
| WO | WO 03/057307 | 7/2003 |
| WO | WO 03/101508 | 12/2003 |

OTHER PUBLICATIONS

Davydov, et al., Vestn. Khir., Sep. 1988—"Vacuum Therapy in the Treatment of Acute Suppurative Diseases of Soft Tissues and Suppurative Wounds" (English translation by R. McElroy Translation Co., Austin, Texas.

Davydov, et al., Khirurglia, Jun. 1990—"Pathogenic Mechanism of the Effect of Vacuum Therapy on the Course of the Wound Process" (English translation by R. McElroy Translation Co., Austin, Texas).

Davydov, et al., Vestn. Khir., Nov. 1986—"Vacuum Therapy in the Treatment of Suppurative Lactation Mastitis" (English translation by R. McElroy Translation Co., Austin, Texas).

Dayydov et al., Vestn. Khir., Oct. 1988—"Bacterlological and Cytological Evaluation of the Vacuum Therapy of Suppurative Wounds" (English translation by R. McElroy Translation Co., Austin, Texas).

Davydov, et al., Vestn. Khir., Mar. 1990—"Basis of the use of Forced Early Secondary Suture in the Treatment of Suppurative Wounds by the Vacuum Therapy Method" (English translation by R. McElroy Translation Co., Austin, Texas).

Mirazimov, et al., Ortop Travmatol Protez., Oct. 1966—"Free Skin Graft of the Foot with Preparation of the Wound Surface by Vacuum Treatment" (English translation by R. McElroy Translation Co., Austin, Texas).

Borzov, et al., Vestn. Dermatol. Venerol., Aug. 1965—"Vacuum Therapy of Some Skin Diseases" (English translation by R. McElroy Translation Co., Austin, Texas).

Jeter, et al., Chronic Wound Care; 27: pp. 240-246—"Managing Draining Wounds and Fistulae: New and Established Methods".

Mulder, et al., Wound Healing Publications 1991—"Clinicians' Pocket Guide to Chronic Wound Repair".

Valenta, AIN Apr. 1994; pp. 44-45—"Using the Vacuum Dressing Alternative for Difficult Wounds".

Wolthuis, et al., Physiological Reviews Jul. 1974; vol. 54, No. 3, pp. 566-595—"Physiological Effects of Locally Applied Reduced Pressure in Man".

Fleischmann, WundForum Spezial IHW 1994; pp. 54-55—"Vacuum Sealing for Treatment of Problematical Wounds" (English translation provided).

Bucalo, et al., Wound Repair and Regeneration; Jul.-Sep. 1993; pp. 181-186—"Inhibition of Cell Proliferation by Chronic Wound Fluid".

Olenius, et al., Plastic and Reconstructive Surgery Feb. 1993: pp. 213-215—"Mitotic Activity in Expanded Human Skin".

Viljanto, et al., Br. J. Surg. 1976; vol. 63: pp. 427-430—"Local Hyperalimentation of Open Wounds".

Dunlop, et al., Br. J. Surg. May 1990; vol. 77: pp. 562-563—"Vacuum Drainage of Groin Wounds after Vascular Surgery: A Controlled Trial".

Comment-Ruckley et al., Apr. 1991, pp. 505-506 on "Vacuum Drainage of Groin Wounds after Vascular Surgery".

Landis, et al., Alternate Suction and Pressure, pp. 925-961—"The Effects of Alternative Suction and Pressure on Blood Flow to the Lower Extremities".

Morykwas, et al., Extracellular Matrix and Healing 1993; pp. 800—"Use of Negative Pressure to Increase the Rate of Granulation Tissue Formation in Chronic Open Wounds".

Svedman, et al., Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds"; Feb. 11, 1999; 16 pages.

Chariker, et al., Contemporary Surgery Jun. 1989; vol. 34: pp. 59-63—"Effective Management of Incisional and Cutaneous Fistulae with Closed Suction Wound Drainage".

Tittel et al., Eingag and Annahme des Manuskripts Jan. 7, 1987; pp. 104-107—"New Standards in Postoperative Wound Drainage".

Genecov, et al., Annals of Plastic Surgery Mar., 1998; vol. 40, No. 3: pp. 219-225—"A Controlled Subatmospheric Pressure Dressing Increases the Rate of Skin Graft Donor Site Reepithelialization".

Morykwas, et al., Annals of Plastic Surgery Jun. 1997; vol. 38, No. 6: pp. 553-562—"Vacuum-Assisted Closure: A New Method for Wound Control and Treatment: Animal Studies and Basic Foundation".

Argenta, et al., Annals of Plastic Surgery Jun., 1997; vol. 38, No. 6: pp. 563-577—"Vacuum-Assisted Closure: A New Method for Wound Control and Treatment: Clinical Experience".

Patent Application and Drawings—"Method of Treating Tissue Damage and Apparatus for Same", consisting of 28 pages.

Nakayama, et al., Ann Plast Surg. May 1991; vol. 26. No. 5: pp. 499-502—"A New Dressing Method for Free Skin Grafting in Hands".

Medical Industry Week—article "KCI Offers New Treatment for Non-Healing Wounds"; 1 page.

Nakayama, et al., Plast. Reconstr. Surg., Dec. 1990.; vol. 86, No. 6: pp. 1216-1219—"A New Method for the Dressing of Free Skin Grats".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).

Teder, et al., J. Invest. Surg.1990; vol. 3: pp. 399-407—"Continuous Wound Irrigation in the Pig".

Wood, et al., Br. J. of Surg.1977; vol. 64: pp. 554-557—"Foam Elastomer Dressing in the Management of Open Granulating Wounds: Experience with 250 Patients".

Neumann, et al., J. of Biomed. Materials Research 1981, vol. 15: pp. 9-18—"Gelatin-Based Sprayable Foam as a Skin Substitute".

Kostluchenok et al., Vestn. Khir. Sep. 1986—"Vacuum Treatment in the Surgical Treatment of Suppurative Wounds" (English translation by R. McElroy Translation Co., Austin, Texas).

Lundvall, et al., Acta Physiol. Scand. 1989. vol. 136: pp. 403-409—"Transmission of Externally Applied Negative Pressure to the Underlying Tissue. A Study on the Upper Arm of Man".

Brochure—Aeros—Instavac Aspirator; 1 page.

Brochure—Pleur-evac Adult-Pediatric-Non-Metered Disposable "3-Bottle" Unit, A-4000; 6 pages.

Brochure—Hiblow Air Pump; 1 page.

Brochure—Aeros—Care-E-Vac; 2 pages.

One page brochure—Aeros—Moblvacll.

Brochure/Instruction Manual—Creative Medical Laboratories, Inc.—TUGS (Transportable Universal Gradient Suction) System.

Brochure—Wells Johnson Company—Point D Aspirator; 2 pages.

Brochure—Microtek Heritage, Inc.—The Wound-Evac ET, Closed Wound Suction System; 4 pages.

Brochure—KCI—The V.A.C. (Vacuum Assisted Closure), Nov. 5, 1998; 7 pages.

Brochure—Augustine Medical, Warm-Up Active Wound Therapy Wound Covers, 1999; 3 pages.
Brochure—Series 55—Emerson Post-Operative Suction Pumps; 1 page.
Brochure—Emerson Transport Suction Unit; 1 page.
US 6,216,701, 4/2001, Heaton et al. (withdrawn).
International Search Report for WO 03/045492 A1, Lockwood et al., Jun. 2003.
Abdullah, BJJ, JHK Coll Radio1, Feb. 21, 2001; vol. 4, pp. 272-273—"A New Method for Fixation of Drainage Catheters".
Amljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).
Blackburn II et al.; "Negative-pressure dressings as a bolster for skin grafts," *Annals of Plastic Surgery*, 40(5):453-457, 1998.
Chinn and Burns, "Closed wound suction drainage," *The Journal of Foot Surgery*, 24(1):76-81, 1985.
Dattilo, Jr. et al.; "Medical Textiles: Application of an Absorbable Barbed Bi-directional Surgical Suture"; *Journal of Textile and Apparel, Technology and Management*, 2(2):1-5, 2002.
Davydov et al., "Concepts for the Clinical-Biological Management of the Wound Process in the Treatment of Purulent Wounds by Means of Vacuum Therapy," *Vestnik Khirurgi*, pp. 132-136 (and 8 page English translation thereof), Jul. 1980.
Davydov et al., "Vacuum Therapy in the Treatment of Purulent Lactation Mastitis," *Vestnik Khirurgi*, pp. 66-70 (and 9 page English translation thereof), May 1986.
Egnell Minor, Instruction Book, First Edition, 300 7502, pp. 24, Feb. 1975.
Egnell Minor: Addition to the Users Manual Concerning Overflow Protection—Concerns all Egnell Pumps, pp. 2, Feb. 1983.
Greer et al., "The use of subatmospheric pressure dressing therapy to close lymphocutaneous fistulas of the groin," *British Journal of Plastic Surgery*, 53(6):484-487, 2000.
Johnson, "An improved technique for skin graft placement using a suction drain," *Surgery, Gynecology, and Obstetrics*, 159(6):584-585, 1984.
Kostyuchenok et al., "Vacuum treatment in the surgical management of purulent wounds," *Vestnik Khirurgi*, pp. 18-21 (and 6 page English translation thereof), Sep. 1986.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," *Journal of Cardiovascular Surgery*, 31:634-639, 1990.
Masters, "Reliable, inexpensive and simple suction dressings," Letter to the Editor, *iBritish Journal of Plastic Surgery*, Elsevier Science/The British Association of Plastic Surgeons, UK, 51(3):267, 1998.
Mendez-Eastman, "When wounds won't heal" *RN*, 61(1):20-24, 1998.
Meyer and V. Schmieden, *Bier's Hyperemic Treatment in Surgery, Medicine, and the Specialties: A Manual of its Practical Application*, (W.B. Saunders Co., Philadelphia, PA 1909), pp. 17-25, 44-64, 90-96, 167-170, and 210-211.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 11/515,983, mailed May 11, 2009.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Oosterbroek et al., "A micromachined pressure/flow-sensor," *Sensor and Actuators*, 77(3):167-177, 1999. Abstract Only.
Orringer et al., "Management of wounds in patients with complex enterocutaneous fistulas," *Surgery, Gynecology & Obstetrics*, 165:79-80, 1987.
PCT International Preliminary Examination Report issued in International Application No. PCT/GB96/02802, mailed Jan. 15, 1998.
PCT International Search Report issued in International Application No. PCT/GB96/02802, mailed Apr. 29, 1997.
PCT International Search Report issued in International Application No. PCT/GB98/02713, mailed Jan. 8, 1999.
PCT International Search Report issued in International Application No. PCT/GB95/01983, mailed Nov. 23, 1995.
PCT Written Opinion issued in International Application No. PCT/GB96/02802, mailed Sep. 3, 1997.
PCT Written Opinion issued in International Application No. PCT/GB98/02713, mailed Jun. 8, 1999.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
Schein et al., "The 'Sandwich Technique' in the management of the open abdomen," *British Journal of Surgery*, 73:369-370, 1986.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary European Search Report, issued in European Application No. EP 02 79 4388, mailed Jun. 16, 2009.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Tennant, "The use of hypermia in the postoperative treatment of lesions of the extremities and thorax," *Journal of the American Medical Association*, 64:1548-1549, 1915.
Tribble, "An improved sump drain-irrigation device of simple construction," *Archives of Surgery*, 105(3):511-513, 1972.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and copy and certified translation), 1986.
Office Communication, issued in Canadian Patent Application No. 2,481,016, dated Aug. 13, 2009.
"Jump-Start Wound Healing with OASIS," *WOUNDS*, Special Supplement, 13(2):1-28, 2001.
"Oasis™ Wound Dressing," *SIS™ Technology*, pp. 1-4, Sep. 2001.
"Surgisis™ Soft-Tissue Graft," *SIS™ Technology*, pp. 1-4, Sep. 2001.
Brochure—"Cavi-Care," *Smith & Nephew*, 2000.
Brochure—Healthpoint® Oasis® Wound Matrix, *Cook Biotech Incorporated*, 2003.
Fourth SIS-ECM Symposium, Phoenix, Arizona, Dec. 6-7, 2002.

Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Letter and Memo reporting Office Action issued in Mexican Application No. PA/a/2001/001124, mailed Jul. 13, 2004.
McCarty, "Cook Incorporated forms dedicated tissue engineered products group," *Cook® Online, News and Media Information*, 2000.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 15, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,623, mailed Jun. 9, 2006.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 10, 2007.
Office Action issued in U.S. Appl. No. 10/524,957, mailed Aug. 3, 2009.
Office Action issued in U.S. Appl. No. 10/524,957, mailed Sep. 30, 2008.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.

Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.
Office Action issued in U.S. Appl. No. 11/230,988, mailed Oct. 3, 2008.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/684,989, mailed Jul. 7, 2009.
Office Action issued in U.S. Appl. No. 11/684,989, mailed Nov. 18, 2008.
PCT Declaration of Non-Establishment of International Search Report issued in International Application No. PCT/US2003/17099, mailed Nov. 7, 2003.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus, First Edition (v 1.3.1), 2007.
Search Report issued in Hungarian Application No. P0103545, mailed Oct. 29, 2001.
Search Report issued in Hungarian Application No. P0500055, mailed May 3, 2005.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Supplementary Search Report issued in European Application No. 08010957.2, mailed Aug. 27, 2008.
Wooding-Scott et al., "No wound is too big for resourceful nurses," RN, pp. 22-25, 1988.
Advisory Action issued in U.S. Appl. No. 10/885,431, mailed Dec. 8, 2009.
Advisory Action issued in U.S. Appl. No. 11/051,283, mailed May 5, 2010.
Advisory Action issued in U.S. Appl. No. 11/515,983, mailed Feb. 1, 2010.
Advisory Action issued in U.S. Appl. No. 11/761,066, mailed Feb. 16, 2010.
Communication of Notice of Opposition issued in European Application No. 07001838.7, mailed Apr. 28, 2010.
Decision on Appeal issued in U.S. Appl. No. 10/276,778, mailed Mar. 6, 2010.
Decision on Appeal issued in U.S. Appl. No. 11/242,543, mailed Mar. 5, 2010.
Notice of Allowance issued in U.S. Appl. No. 10/276,778, mailed May 21, 2010.
Notice of Allowance issued in U.S. Appl. No. 10/664,535, mailed Jun. 2, 2010.
Notice of Allowance issued in U.S. Appl. No. 10/885,431, mailed Mar. 22, 2010.
Notice of Allowance issued in U.S. Appl. No. 11/761,066, mailed May 13, 2010.
Office Action issued in Canadian Application No. 2,481,016, mailed Jun. 15, 2010.
Office Action issued in Japanese Application No. 2001-539532, mailed May 11, 2010 (and English language translation thereof).
Office Action issued in Japanese Application No. 2004-508861, mailed Feb. 16, 2010 (and English language translation thereof).
Office Action issued in U.S. Appl. No. 10/524,957, mailed Feb. 25, 2010.
Office Action issued in U.S. Appl. No. 10/524,957, mailed Jul. 26, 2010.
Office Action issued in U.S. Appl. No. 10/664,535, mailed Dec. 15, 2009.
Office Action issued in U.S. Appl. No. 11/051,283, mailed Feb. 25, 2010.
Office Action issued in U.S. Appl. No. 11/230,988, mailed May 26, 2010.
Office Action issued in U.S. Appl. No. 11/515,983, mailed May 7, 2010.
Office Action issued in U.S. Appl. No. 11/515,983, mailed Nov. 20, 2009.
Office Action issued in U.S. Appl. No. 11/684,989, mailed Dec. 29, 2009.
Office Action issued in U.S. Appl. No. 11/684,989, mailed Jun. 29, 2010.
Office Action issued in U.S. Appl. No. 11/761,066, mailed Dec. 9, 2009.
Supplemental Notice of Allowability issued in U.S. Appl. No. 10/885,431, mailed Apr. 22, 2010.
Notice of Allowance issued in U.S. Appl. No. 10/276,778, mailed Sep. 7, 2010.
Notice of Allowance issued in U.S. Appl. No. 10/524,957, mailed Oct. 14, 2010.
Notice of Allowance issued in U.S. Appl. No. 10/664,535, mailed Sep. 9, 2010.
Notice of Allowance issued in U.S. Appl. No. 11/242,543, mailed Sep. 27, 2010.
Notice of Allowance issued in U.S. Appl. No. 11/684,989, mailed Nov. 8, 2010.

Office Action issued in European Application No. 01 998 292.5, mailed May 7, 2010.
Office Action issued in European Application No. 02 794 397.6, mailed Oct. 12, 2010.
Office Action issued in Japanese Application No. 2008-007788, mailed Oct. 5, 2010.
Office Action issued in U.S. Appl. No. 11/051,283, mailed Oct. 15, 2010.
Office Action issued in U.S. Appl. No. 11/230,988, mailed Oct. 15, 2010.
Office Action issued in U.S. Appl. No. 11/515,983, mailed Oct. 5, 2010.
Response to Opposition submitted in European Patent No. EP 1 772 160, filed Sep. 29, 2010.
Notice of Allowance issued in U.S. Appl. No. 11/515,983, mailed May 17, 2011.
Office Action issued in European Application No. 02 794 392.7, mailed May 3, 2011.
Office Action issued in European Application No. 02 794 394.3, mailed Jun. 14, 2011.
Office Action issued in Japanese Application No. 2008-007788, mailed Jun. 28, 2011. (English translation).
Office Action issued in Japanese Patent Application No. 2009-236963, dated Aug. 2, 2011. (English translation).
Office Action issued in U.S. Appl. No. 12/328,531, mailed Jun. 13, 2011.
Notice of Allowance issued in U.S. Appl. No. 11/051,283, mailed Mar. 29, 2011.
Notice of Allowance issued in U.S. Appl. No. 11/230,988, mailed Dec. 3, 2010.
Office Action issued in Canadian Application No. 2,481,016, mailed Apr. 1, 2011.
Office Action issued in European Application No. 02 794 388.5, mailed Feb. 10, 2011.
Office Action issued in European Application No. 02 794 394.3, mailed Nov. 26, 2010.
Office Action issued in European Application No. 03 734 294.6, mailed Apr. 21, 2011.
Office Action issued in Japanese Application No. 2008-007788, mailed Oct. 5, 2010.
Office Action issued in U.S. Appl. No. 12/860,581, mailed Apr. 29, 2011.

* cited by examiner

US 8,168,848 B2

ACCESS OPENINGS IN VACUUM BANDAGE

CROSS-REFERENCE TO RELATED APPLICATIONS

This application is a U.S. national counterpart application of international application serial no. PCT/US02/41210 filed Dec. 20, 2002, which claims the benefit of U.S. provisional application Ser. No. 60/371,618 filed Apr. 10, 2002.

BACKGROUND OF THE INVENTION

The present disclosure relates to bandages for wounds, and more particularly to bandages for use with a vacuum and/or irrigation source.

The prior art contemplates that chronic wounds may be treated by providing a vacuum in the space above the wound to promote healing. A number of prior art references teach the value of the vacuum bandage or the provision of vacuum in the space above the surface of a chronic wound.

A vacuum bandage is a bandage having a cover for sealing about the outer perimeter of the wound and under which a vacuum is established to act on the wound surface. Applying vacuum to the wound surface promotes healing of chronic wounds. Typically, suction tubes are provided for drawing exudate away from the wound and for creating vacuum under the cover. If the cover is a flexible cover, which is typically more comfortable for the patient, a porous packing may be provided under the cover to fill the space in which the vacuum is formed. It will be appreciated, however, that the packing will be omitted by many caregivers, and it may be preferable not to have packing. The following U.S. patents establish the nature of vacuum treatment bandages and devices: U.S. Pat. Nos. 6,095,992, 6,080,189, 6,071,304, 5,645,081, 5,636,643, 5,358,494, 5,298,015, 4,969,880, 4,655,754, 4,569,674, 4,382,441, and 4,112,947. All of such references are incorporated herein by reference for purposes of disclosing the nature of such vacuum treatment of wounds.

As shown, for example, in U.S. Pat No. 5,645,081 (hereinafter the '081 patent), a method of treating tissue damage is provided by applying negative pressure to a wound. The negative pressure is provided in sufficient duration and magnitude to promote tissue migration in order to facilitate the closure of the wound. FIG. 1 of the '081 patent discloses an open cell polyester foam section covering the wound, a flexible hollow tube inserted into the foam section at one end and attached to a vacuum pump at another end, an adhesive sheet overlying the foam section, and tubing to adhere to the skin surrounding the wound in order to form a seal that allows the creation of a vacuum when the suction pump is operating. The '081 patent further teaches use of negative pressure between about 0.1 and 0.99 atmospheres and that the pressure can be substantially continuous and is relieved only to change the dressing on the wound. Alternatively, the '081 patent teaches use of a cyclic application of pressure in alternating periods of application and non-application. In a preferred embodiment, pressure is applied in five-minute periods of application and non-application.

Various other prior art references teach the value of the vacuum bandage or the provision of vacuum to the surface of a chronic wound. Several Russian language articles exist which establish the efficacy of vacuum therapy in the 1980's. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., September 1988 (The September 1988 article); "Pathenogenic mechanism of the effect of vacuum therapy on the course of the wound process", Davydov, et al. Khirurigiia, June 1990 (the June 1990 article); and "Vacuum therapy in the treatment of suppurative lactation mastitis", Davydov, et al. Vestn. Khir., November 1986 (the November 1986 article).

The Russian articles distinguish wound drainage from use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8-1 atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76-114 mmHg. The Russian articles teach using this vacuum method to decrease the number of microbes in the wound. The June 1990 Russian article teaches that this vacuum therapy provides a significant antibacterial effect. The article describes the stepped up inflow of blood to the zone around the wound to lead to an increase in the number of leukocytes reaching the focus of inflammation. Subsequent articles and patents further develop the benefits obtained with vacuum therapy.

SUMMARY OF THE INVENTION

The present invention comprises one or more of the following features, discussed below, or combinations thereof:

A member for use with a wound having a wound surface is provided. The member is also provided for use in a vacuum bandage connected to a vacuum source. The member may include a top surface and a bottom surface adapted to be in contact with and generally conform to the wound surface. The member may further include a plurality of discrete holes formed in the bottom surface and at least one discrete opening formed in the top surface. The member may include a port communicating with the vacuum source, each discrete hole, and at least one discrete opening.

The member may include a wound contacting layer, or wound contactable layer, having channels formed therein and a cover coupled to the wound contacting layer to cooperate with the channels of the wound contacting layer to define a set of passageways.

The cover may have a first surface area and the wound contacting layer may have a second surface area that is larger than the first surface area. The channels of the wound contacting layer may extend beyond an outer edge of the cover to define the plurality of discrete openings in an outer peripheral portion of the member.

The cover may include a plurality of discrete holes in communication with the channels of the wound contacting layer to define the plurality of discrete openings of the member.

Features of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 2:
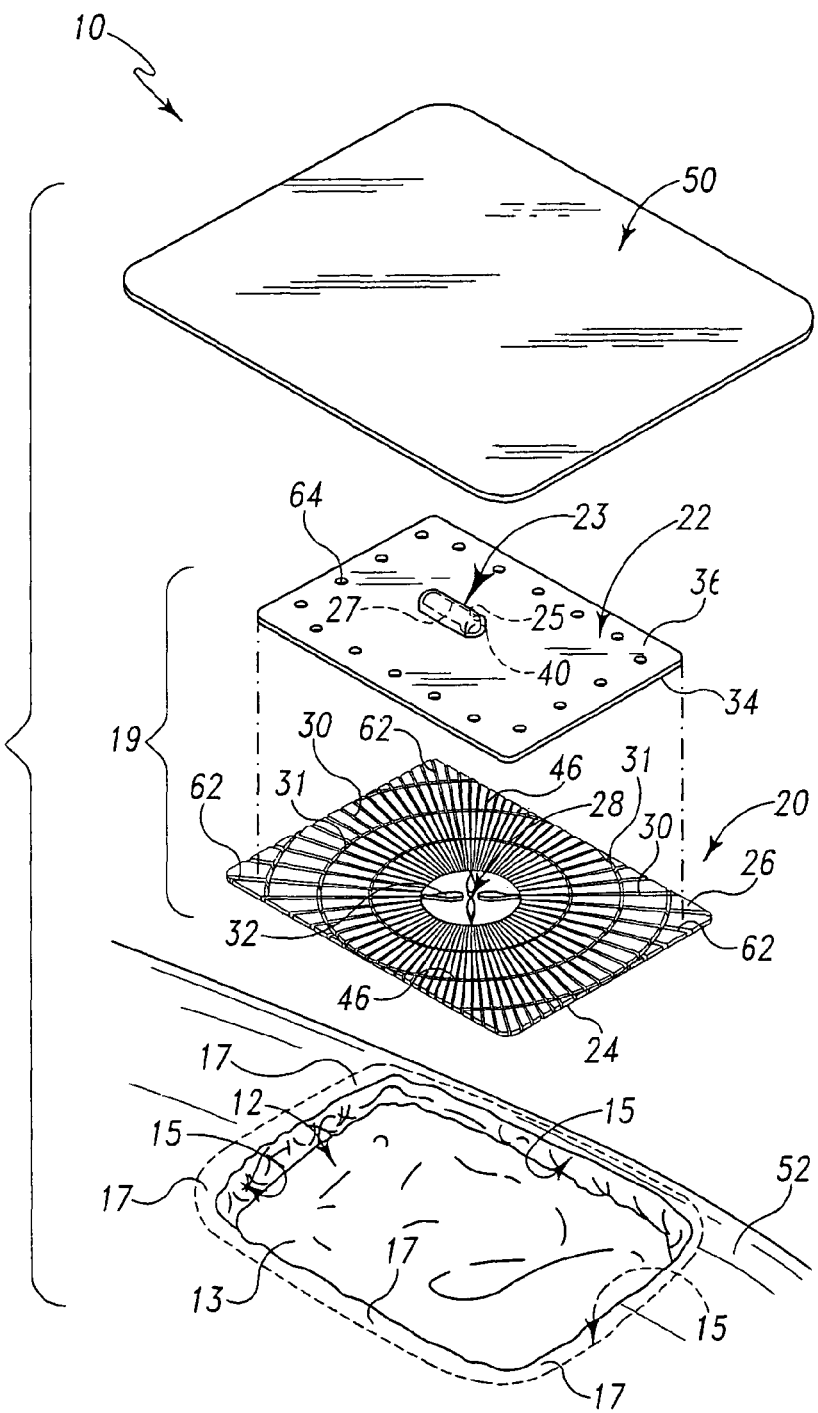
FIG. 2 is an exploded perspective view of the wound care bandage positioned above a wound bed showing a wound contacting layer and a cover of the bandage which cooperate to form a wound dressing member for placement within the wound bed, and showing the member having a top surface with peripheral openings that communicate negative pressure to tissue that overhangs areas of undermining in the wound.
Figure 4:
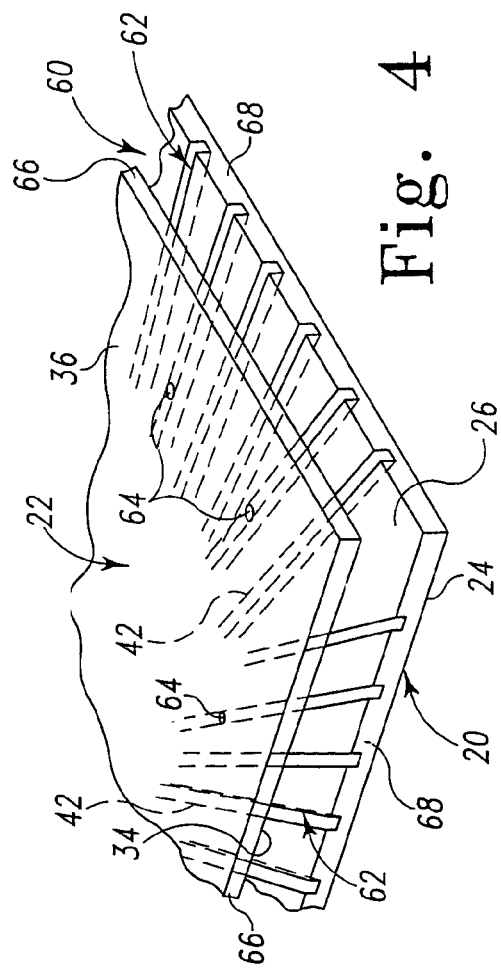
FIG. 4 is a perspective view of a portion of the member of the bandage showing the peripheral openings of the member.

A vacuum bandage 10 is provided for use with a wound 12 having a wound surface 13, shown in FIG. 2. Vacuum bandage 10 includes a thin, flexible wound dressing member 19 having upper peripheral discrete access openings (including discrete access channels 62 and discrete access holes 64) to allow member 19 to communicate with the wound surface 13 of wound 12 and with undermined portions 15 of wound 12. Member 19 includes a wound contacting layer, or wound contactable layer, 20 and a cover 22 coupled to the layer 20. Cover 22 is smaller than layer 20 to create access channels 62, as shown in FIG. 4. Member 19 also includes a connector 23 coupled to cover 22 for communication with vacuum source 14 and/or irrigation source 16. Bandage 10 further includes a sealing layer film, or outer cover 50 to be placed over member 19 and wound 12 to seal about the wound 12 to a patient's healthy skin 52 to create a sealed environment between wound surface 13 and outer cover 50.

Figure 1:
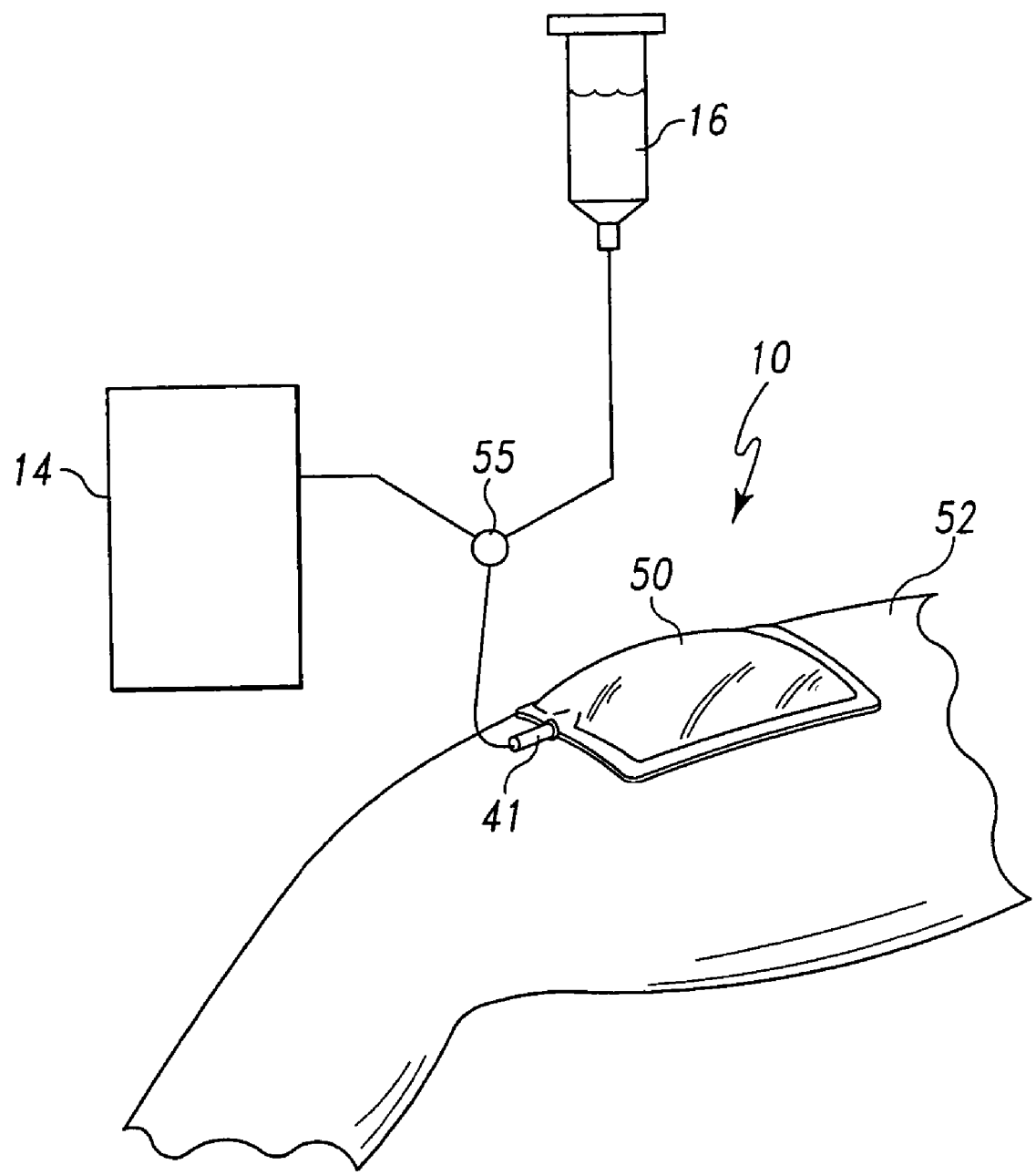
FIG. 1 is a part perspective and part diagrammatic view of a wound care bandage showing the wound care bandage located on the leg of a patient and coupled to both a vacuum source and an irrigation source through the use of a switch valve.

Vacuum bandage 10 is provided for use with a vacuum source 14 and an irrigation source 16 through the use of a switch valve 55, as shown in FIG. 1. Bandage 10 promotes the healing of wound 12, including undermined portions 15 of wound 12, by providing vacuum therapy to the wound 12 and undermined portions 15 of the wound 12 to promote blood flow and remove exudate from wound surface 13 and by providing for irrigation of the wound 12 with fluids such as saline, for example. An illustrative wound treatment apparatus having a wound temperature control system, a medicine delivery system, and a drainage system is disclosed in U.S. Pat. No. 6,458,109. An illustrative vacuum and irrigation system is disclosed in U.S. Patent Publication No. US 2002/0161317 A1. Additionally, an illustrative vacuum bandage is disclosed in U.S. Patent Publication No. US 2002/0065494 A1. Alternative vacuum bandages are disclosed in U.S. Patent Publication No. US 2002/0082567 A1 All of these applications are hereby incorporated herein by reference.

As stated above, access openings 62, 64 are provided to allow vacuum suction and irrigation to be dispensed on the top as well as the bottom of member 19, as is described in more detail below. As shown in FIG. 4, access openings include both access channels 62 and access holes 64. It is also within the scope of this disclosure for member 19 to include either access channels 62 or access holes 64 formed in a top surface of member 19. Access openings 62, 64 are especially beneficial for undermined wounds. Undermined wounds are wounds in which a portion of the sides or side walls of the wound have been eroded away such that a portion of tissue 17 is left overhanging the area 15 that has eroded.

Referring now to FIG. 2, layer 20, cover 22, and connector 23 of member 19 are each made of a medical grade silicone or other type of pliable elastomer. Two companies, for example, which manufacture such medical grade silicone are GE Silicones and NuSil Technology. It is within the scope of this disclosure, however, to include a member made of any type of thin, flexible material that is non-porous and non-foam-like. This thin, flexible material is also generally non-absorptive. For example, materials such as polyvinylchloride (PVC), PVC free of diethylhexyl phthalate (DEHP-free PVC), polyurethane, or polyethylene may be used in the manufacture of member 19. Further, layer 20, cover 22, and connector 23 may each be molded to include anti-microbial constituents. For example, it is within the scope of this disclosure to impregnate member 19 with silver ions which are known anti-microbials.

Figure 3:
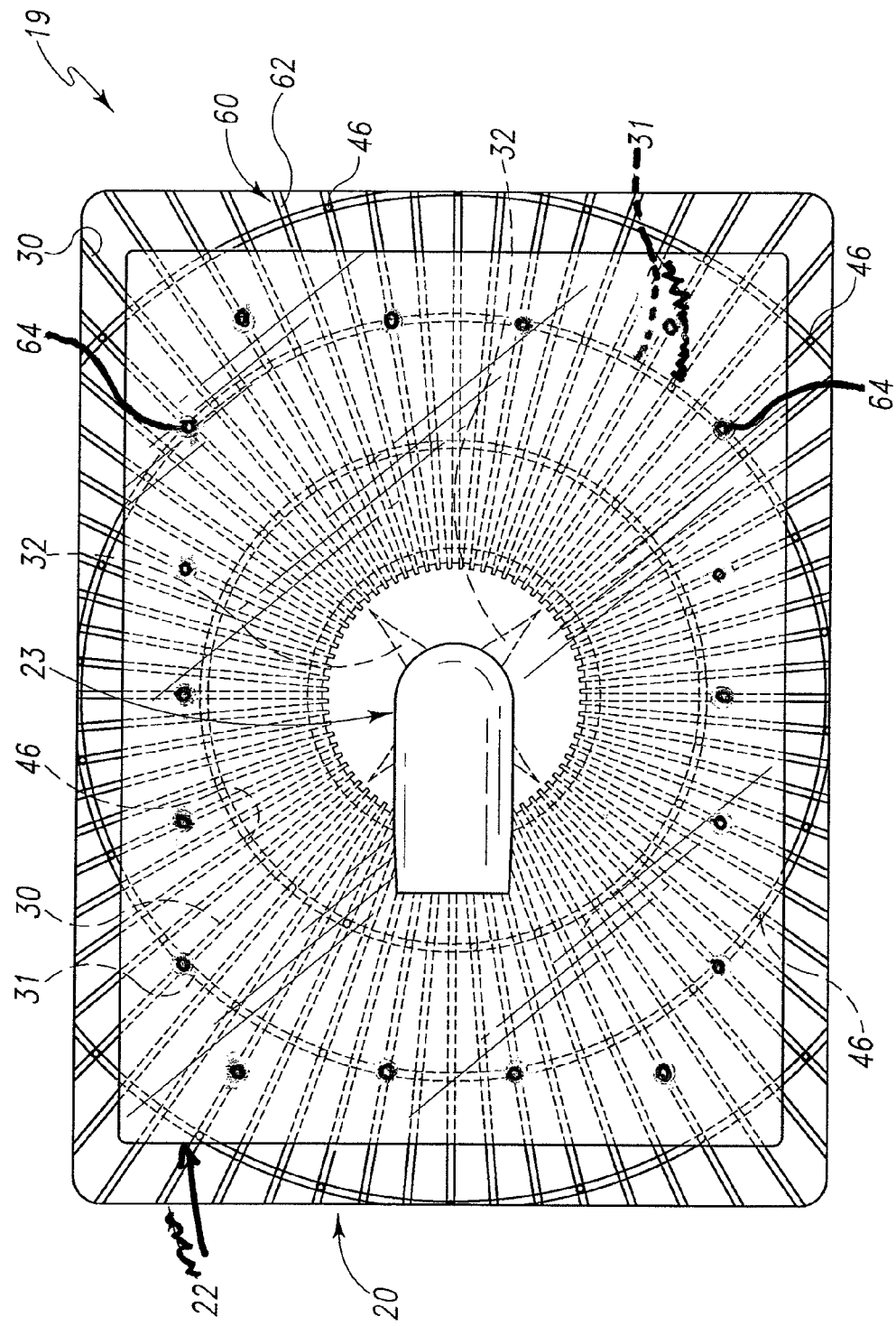
FIG. 3 is a top plan view of the member of the bandage showing the cover of the member being smaller than the wound contacting layer of the member in order to expose peripheral openings of the member.

Member 19, including layer 20, cover 22, and connector 23, is also made of a generally non-adhesive material. Therefore, wound contacting layer 20, which lies adjacent to the wound surface 13, does not adhere to the wound surface 13. Further, member 19 is solid in nature and generally non-compressible. Member 19 is also transparent, as shown in FIG. 3. Therefore, a caregiver or user is able to see the wound 12 through member 19 when member 19 is placed adjacent to wound surface 13. This transparency allows the caregiver to view the progress of the healing of the wound 12.

Layer 20 includes or wound contacting surface 24 and an upper or opposite surface 26. Wound contacting surface 24, or portions thereof, contact and generally conform to the wound surface 13. Opposite surface 26 includes a central area 28 and a plurality of channels 30 spaced-apart from and extending radially away from central area 28. Central area 28 is recessed relative to the portions of upper surface 26 between channels 30. As shown in FIGS. 3 and 4, channels 30 are open at the sides and ends of member 19. As is described below, channels 30 form access channels 62 at the periphery of member 19. Opposite surface 26 further includes concentric channels 31. Illustratively, each channel 30 is 0.030 inch (0.762 mm) wide and 0.030 inch (0.762 mm) deep. It is within the scope of this disclosure, however, to include channels 30, 31 of opposite surface 26 having various widths and depths suitable for the present application. Central area 28 of layer 20 is provided to communicate with the vacuum source 14 and irrigation source 16 through a port 40 of cover 22, as will be described below.

Figure 5:
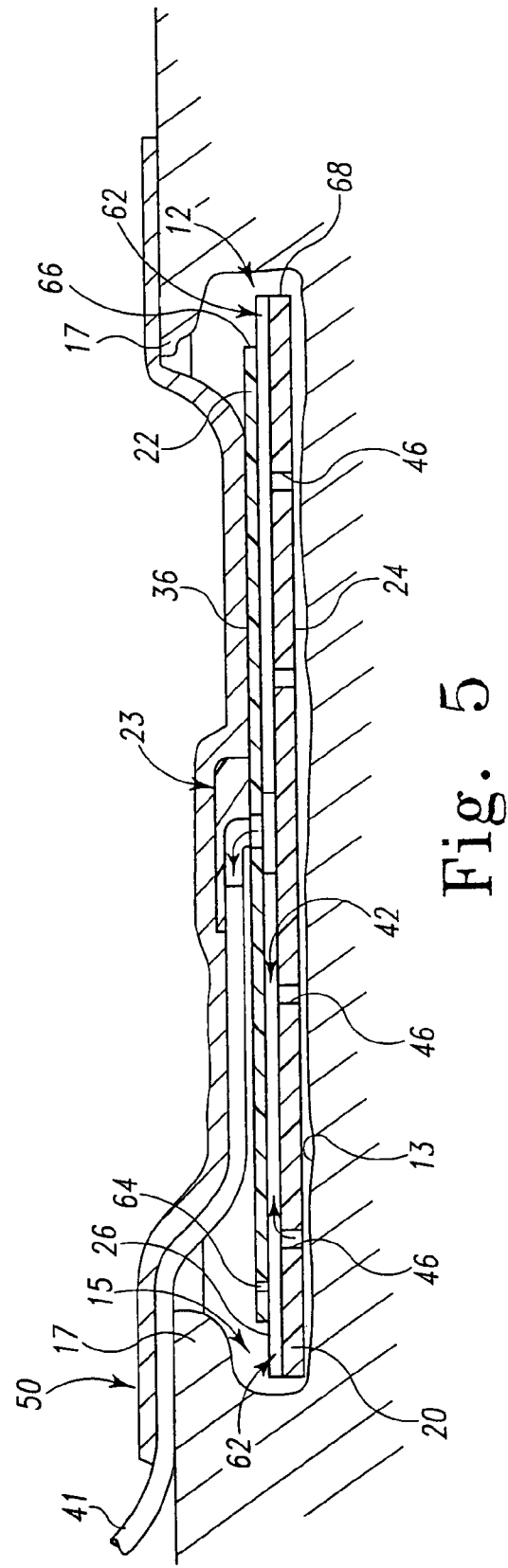
FIG. 5 is a sectional view of the bandage over the wound showing tissue overhanging the peripheral openings in communication with undermined portions of the wound in order to provide suction and irrigation to the areas of undermining.

A plurality of radially extending protrusions or bosses 32 are positioned around central area 28. Bosses 32 are positioned between central area 28 and channels 30, 31, as shown in FIG. 1. Bosses 32 are provided to prevent central area 28 from collapsing in on port 40 of cover 22 to form a seal and effectively block air flow through port 40 while suction is applied to the bandage 10. Port 40 communicates with the vacuum source 14 and/or the irrigation source 16 via connector 23 and tube 41, as shown in FIGS. 1 and 2. As shown in FIG. 5, tube 41 is coupled directly to connector 23. In some embodiments, tube 41 may be coupled to connector 23 by a barbed tube coupler (not shown) engaged with tube 41 and connector 23 to provide a fluid connection therebetween.

As mentioned above, port 40 is in communication with central area 28 of layer 20. Illustratively, four bosses 32 are shown in FIG. 1. However, it is within the scope of this disclosure to provide any number of bosses 23 or the like around central area 28 of layer 20 to prevent central area 28 from sealing off port 40 of cover 22 as suction is applied to bandage 10. Further, it is within the scope of this disclosure to include a boss or bosses having any shape in order to prevent central area 28 from sealing off port 40 when vacuum source 14 is running.

Connector 23, as shown in FIGS. 1 and 2 is a tubal port coupled to a top surface 36 of cover 22 and in communication with port 40 of cover 22. As mentioned before, it is within the scope of this disclosure for connector 23 to be a separate component of member 19 which is coupled to cover 22 or for connector 23 to be coupled to cover 22 by being molded integrally with cover 22. Connector 23 includes a passageway formed at a right-angle. Thus, the passageway in connector 23 has a vertical portion 25 that communicates with port 40 and a horizontal portion 27 that communicates with vertical portion 25. Connector 23 may also be molded to include a single passageway positioned at an angle with respect to cover 22. Connector 23 connects with tube 41 to provide a horizontal tube attachment for tube 41. Cover 22 includes a bottom surface 34 and top surface 36, as shown in FIG. 1. Bottom surface 34 engages opposite surface 26 of layer 20, as shown in FIG. 2.

In some embodiments, member 19 is formed by heat sealing opposite surface 26 of layer 20 and bottom surface 34 of cover 22 together and by heat sealing connector 23 to top surface 36 of cover 22. For example, each of connector 23, cover 22 (or the combination of cover 22 and connector 23), and layer 20 may be pre-shaped and formed from semi-cured silicone. Once the connector 23, cover 22, and layer 20 are placed together appropriately, the entire member 19 may be heated to heat seal and cure each of the three components to one another. Alternatively, for example, the cover 22 only may be made from semi-cured silicone while the connector 23 and layer 20 may be made from fully cured silicone. Once placed together and heated, connector 23 and layer 20 will heat seal to cover 22. Semi-cured silicone may be bought and pre-molded from a manufacturer such as NuSil Technology, for example.

Although the method of heat sealing the cover 22, connector 23, and layer 20 to each other is disclosed, it is within the scope of this disclosure to form member 19 by coupling layer 20, cover 22, and connector 23 together by any other suitable means such as through the use of adhesives, for example. Further, it is within the scope of this disclosure to provide a member 19 where cover 22 lies adjacent to, but is not coupled to, layer 20.

As mentioned above, cover 22 is coupled to layer 20 and connector 23 is coupled to cover 22 to form member 19. Cover 22 and layer 20 cooperate to form discrete passageways 42 of member 19 defined by channels 30, 31 of layer 20 and bottom surface 34 of cover 22, as shown in FIG. 5. Passageways 42 extend from an outer edge 66 of cover 22 and are in communication with central area 28 of layer 20. Illustratively, cover 22 has a first surface area and layer 20 has a second surface area larger than the first surface area. Therefore, outer portions of radial channels 30 extend between outer edge 66 of cover 22 and outer edge 68 of layer 20 to define peripheral access channels 62 for providing vacuum suction or irrigation to undermined portions 15 of wound 12. Central area 28 of layer 20 is in communication with port 40 of cover 22 which is in communication with the vacuum and/or irrigation sources 14, 16, via connector 23, and tube 41. Therefore, peripheral access channels 62 are in communication with the vacuum and/or irrigation sources 14, 16 via passageways 42.

Layer 20 includes through holes 46 which extend from channels 30, 31 to wound contacting surface 24, as shown best in FIG. 5. Holes 46 are discrete and are provided to communicate with channels 30, 31 of layer 20. Holes 46 therefore communicate with passageways 42 of member 19 and the vacuum and/or irrigation sources 14, 16 as well to allow the suction from the vacuum source 14 and/or the fluid from the irrigation source 16 to reach the wound bed surface 13 via the holes 46. Illustratively, holes 46 are 0.020 inch (0.508 mm) in diameter and are spaced approximately 0.500 inch (12.700 mm) apart along channels 30, 31 of layer 20. It is, however, within the scope of the disclosure to include holes having other suitable sized diameters and/or other suitable spacing that allow for the removal of exudate without generally clogging.

As mentioned above, member 19 further includes peripheral access holes 64. Specifically, holes 64 are formed through cover 22 and are positioned near outer edge 66, as shown in FIG. 4. Holes 64 are in communication with passageways 42 to provide either suction or irrigation to undermined portions 15 of wound 12. Although member 19 is shown to include both peripheral access channels 62 and peripheral access holes 64, it is within the scope of this disclosure to include a member having either peripheral access channels 62 or peripheral access holes 64. Further, it is within the scope of this disclosure to include a member having other suitable access openings in addition to or in replacement of channels 62 and holes 64. As shown in FIG. 5, undermined portions 15 of wound 12 are in communication with peripheral access openings 62, 64 to directly expose undermined portions 15 to suction and irrigation treatment. Furthermore, member 19 can be manufactured to have sizes (i.e., thickness, length, width, etc.) and/or shapes (rectangular, square, triangular, round, etc.) other than those shown for use in wounds of various sizes and shapes. The member 19 may be cut to fit wound 12 to lie at the bottom of wound 12 adjacent wound surface 13.

It is within the scope of this disclosure to include an adhering, but removable, piece of disposable paper on the top surface of member 19 so that a caregiver may trace the shape of the wound 12 onto the paper and cut the member 19 to fit wound 12. Further, member 19 may be trimmed to leave a space of ¼ inch (6.35 mm) to ½ inch (12.7 mm) or greater between the cut outer edge of member 19 and an inner boundary edge of wound 12. It is not necessary for member 19 to be in contact with the entire wound surface 13. As shown in FIG. 5, member 19 is sized to fit under overhanging tissue 17 into undermined areas 15 of wound 12. Member 19 may also be trimmed so that certain portions of member 19 are sized to fit into irregular undermined areas 15 of a wound.

Member 19, including layer 20, cover 22, and connector 23, includes a top surface and a bottom surface. The bottom surface of member 19 is wound contacting surface 24 of layer 20. The top surface of member 19, however, includes top surface 36 of cover 22 and the portion of upper or opposite surface 26 of layer 20 positioned between outer edge 66 of cover 22 and outer edge 68 of layer 20. Therefore, the access openings (including access channels 62 of layer 20 and access holes 64 of cover 22) are formed in the top surface of member 19.

As mentioned above, bandage 10 further includes a sealing layer or film 50 that is placed over cover 22 and around tube 41, as shown in FIG. 2. Film 50 acts as an outer cover of the bandage 10 and covers the entire wound 12 by extending over wound 12 and attaching to the patient's healthy skin 52, also as shown in FIG. 2. Preferably, film 50 is an occlusive or semi-occlusive material which allows water vapor to permeate through. Because of this characteristic, the film 50 is referred to as Moisture Vapor Transmission Rate film or MVTR film. The products TEGADERM brand sealing film made by 3M Corporation, and OPSITE FLEXIGRID semi-permeable dressing made by Smith & Nephew can be used for film 50, for example. Film 50 is approximately 0.003 inch (0.076 mm) thick. However, it is within the scope of this disclosure to include any occlusive or semi-occlusive film 50 having another thickness. Film 50 is provided to create a sealed environment below the film 50 and around the wound 12 in which a vacuum or negative pressure can be maintained as provided by vacuum source 14. Film 50 therefore creates a vacuum space 53 below film 50 and above wound surface 13.

As shown in FIG. 2, sealing film 50 is positioned adjacent top surface 36 of cover 22. It is within the scope of this disclosure, however, for bandage 10 to further include a packing material or filler such as gauze, for example, positioned between film 50 and member 19.

As shown in FIG. 5, member 19 of bandage 10 has a smooth wound contacting surface 24. Wound contacting surface 24 may also be textured or roughened and/or may include a rib, protrusion, channel, or spacer design. By providing member 19 with a rib, protrusion, channel, or spacer, a space is created between surface 24 of layer 20 and wound surface 13. Through holes 46 communicate with this space to permit vacuum source 14 to establish a generally uniformly distributed vacuum or negative pressure to the wound surface 13 and to overhanging tissue 17 to draw blood from the body to the wound surface 13 and to overhanging tissue 17 and to draw exudate from the wound 12 through holes 46 and openings 62, 64, into channels 30, 31 and passageways 42, and out port 40 of cover 22.

The vacuum or negative pressure, which draws blood from the body to the wound surface 13 and draws exudate from the wound 12 up through member 19, promotes the healing of wound 12. The negative pressure is distributed to a bottom portion of wound 12 through holes 46 and is distributed to undermined areas 15 and overhanging tissue 17 of the wound 12 through openings 62, 64 to draw exudate from these areas of the wound 12 through passageways 42 and out port 40 of member 19. As wound 12 heals, granulations form along the wound surface 13. Granulations, therefore, are the replacement within the wound bed of tissue lost. As the granulations fill in the wound bed causing the wound 16 to heal, member 19 rides up on the wound surface 13 on top of the granulations which are formed.

As mentioned above, port 40 of cover 22 communicates with vacuum source 14 and/or irrigation source 16 via connector 23 and tube 41. As shown in FIG. 1, a switch valve 55 is provided which allows the caretaker to switch between the use of the vacuum source 14 and the irrigation source 16. It will be appreciated that a mechanism other than the switch valve 55 maybe used selectively to couple the vacuum source 14 or the irrigation source 16 to the bandage 10. Simple tube clamps, for example, may be used selectively to open and close the tube set provided with bandage 10. When valve 55 is switched to operate the vacuum source 14, the vacuum suction draws exudate up through holes 46 and openings 62, 64, radially inwardly through passageways 42 toward port 40, and finally through connector 23 and tube 41. Although tube 41 has been referred to as vacuum tube 41, tube 41 may also be used as an irrigation tube carrying liquid to the wound 12 from irrigation source 16, as described above.

Although this invention has been described in detail with reference to certain embodiments, variations and modifications exist within the scope and spirit of the invention as described and defined in the following claims.

The invention claimed is:

1. A member for use in a vacuum bandage connected to a vacuum source and for use with a wound having a wound surface, the member comprising
    a wound contactable layer having a bottom surface adapted to be in contact with and generally conform to the wound surface,
    a plurality of discrete holes extending through the bottom surface of the wound contactable layer,
    a generally non-porous cover coupled to the wound contactable layer,
    at least one discrete opening extending through a top surface of the cover such that the at least one discrete opening is configured to communicate negative pressure directly to an undermined portion of the wound, and
    a port configured to communicate with the vacuum source, the port being in fluid communication with each discrete hole and the at least one discrete opening.

2. The member of claim 1, wherein the wound contactable layer has a top surface having a plurality of channels formed therein, and wherein the cover has a bottom surface that engages with the top surface of the wound contactable layer and cooperates with the channels formed in the top surface of the wound contactable layer to define a plurality of passageways between the port and each discrete hole and between the port and the at least one discrete opening.

3. The member of claim 2, wherein the cover has a first surface area and the wound contactable layer has a second surface area larger than the first surface area, and wherein the channels of the wound contactable layer extend beyond an outer edge of the cover.

4. The member of claim 2, wherein the at least one discrete opening comprises a plurality of discrete openings in communication with the channels of the wound contactable layer.

5. The member of claim 1, wherein the at least one discrete opening comprises a plurality of discrete openings extending through the top surface of the cover and adapted to communicate negative pressure to undermined portions of the wound.

6. The member of claim 5, wherein the cover includes an outer peripheral portion and the plurality of discrete openings are formed in the outer peripheral portion of the cover.

7. The member of claim 6, wherein the member is relatively thin and flexible.

8. A bandage connectable to a vacuum source for use with a wound having a wound surface, the bandage comprising
    a port configured to communicate with the vacuum source,
    a wound contactable layer having a bottom surface adapted to be in contact with and generally conform to the wound surface, a plurality of discrete channels extending along a top surface of the wound contactable layer, the channels being in communication with the port, and a plurality of discrete holes opening through the bottom surface of the wound contactable layer, and
    a cover coupled to the wound contactable layer and having a generally continuous planar bottom surface which extends between an outer perimeter of the cover, wherein a majority of the generally continuous planar bottom surface is directly engaged with the top surface of the wound contactable layer such that the cover cooperates with the channels extending along the top surface of the wound contactable layer to define a plurality of passageways connecting each hole with the port, the bottom surface of the cover having a first surface area and the top surface of the wound contactable layer having a second surface area larger than the first surface area such that outer portions of the channels extend between an outer edge of the cover and an outer edge of the wound contactable layer to define a plurality of peripheral access channels configured to communicate negative pressure to an undermined portion of the wound, the cover configured to substantially prevent communication of negative pressure through the bottom surface of the cover.

9. A member for use in a vacuum bandage connected to a vacuum source and for use with a wound having a wound surface, the member comprising a port configured to communicate with the vacuum source, a wound contactable layer having a bottom surface adapted to be in contact with and generally conform to the wound surface, a plurality of discrete channels extending along a top surface of the wound contactable layer, the channels being in communication with the port, a first plurality of discrete holes opening through the bottom surface of the wound contactable layer and adapted to communicate negative pressure to the wound surface, and a generally non-porous cover coupled to the wound contactable layer, a second plurality of discrete holes extending through a top surface of the cover, the cover having a bottom surface cooperating with the channels extending along the top surface of the wound contactable layer to define a plurality of passageways connecting each first discrete hole and each second discrete hole with the port, the bottom surface of the cover having a first surface area and the top surface of the wound contactable layer having a second surface area larger than the first surface area such that outer portions of the channels extend between an outer edge of the cover and an outer edge of the wound contactable layer to define a plurality of peripheral access channels, the second plurality of discrete holes and the plurality of peripheral access channels configured to communicate negative pressure directly to an undermined portion of the wound.

10. The member of claim 9, wherein the member is relatively thin and flexible.

11. The member of claim 10, wherein the cover includes an outer peripheral portion and the second plurality of discrete holes are formed in the outer peripheral portion.

* * * * *

UNITED STATES PATENT AND TRADEMARK OFFICE
CERTIFICATE OF CORRECTION

PATENT NO. : 8,168,848 B2
APPLICATION NO. : 10/509137
DATED : May 1, 2012
INVENTOR(S) : Jeffrey S. Lockwood et al.

It is certified that error appears in the above-identified patent and that said Letters Patent is hereby corrected as shown below:

In title page, item (56) References Cited - U.S. PATENT DOCUMENTS, insert
--6,264,979 B1    7/2001--.

In title page, item (56) References Cited - FOREIGN PATENT DOCUMENTS, insert
--EP   0 880 953 A2    12/1998
WO   00/26100         5/2000
WO   00/30567         6/2000--.

Signed and Sealed this
Ninth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,168,848 B2
APPLICATION NO. : 10/509137
DATED : May 1, 2012
INVENTOR(S) : Jeffrey S. Lockwood et al.

Page 1 of 1

It is certified that error appears in the above-identified patent and that said Letters Patent is hereby corrected as shown below:

On the title page, item (73) Assignee, delete "KCI Medical Resources, Inc." and insert --KCI Medical Resources-- therefor.

Signed and Sealed this
Twelfth Day of November, 2013

Teresa Stanek Rea
*Deputy Director of the United States Patent and Trademark Office*